United States Patent
Stjernschantz et al.

[11] Patent Number: 6,031,001
[45] Date of Patent: *Feb. 29, 2000

[54] USE OF PROSTAGLANDINS

[75] Inventors: Johan Stjernschantz; Bahram Resul, both of Uppsala, Sweden

[73] Assignee: Synphra AB, Uppsala, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/809,017

[22] PCT Filed: Sep. 19, 1995

[86] PCT No.: PCT/SE95/01059

§ 371 Date: May 16, 1997

§ 102(e) Date: May 16, 1997

[87] PCT Pub. No.: WO96/09055

PCT Pub. Date: Mar. 28, 1996

[30] Foreign Application Priority Data

Sep. 21, 1994 [SE] Sweden ................................. 9403158

[51] Int. Cl.$^7$ ................................................. A61K 31/557
[52] U.S. Cl. ............................................................. 514/573
[58] Field of Search ................................................ 514/573

[56] References Cited

U.S. PATENT DOCUMENTS

| | | | |
|---|---|---|---|
| 4,009,282 | 2/1977 | Voorhees | 424/317 |
| 4,024,174 | 5/1977 | Hayashi et al. | 260/468 D |
| 4,254,145 | 3/1981 | Birnbaum | 424/305 |

FOREIGN PATENT DOCUMENTS

| | | |
|---|---|---|
| 0097023 | 12/1983 | European Pat. Off. . |
| 0242580 | 10/1987 | European Pat. Off. . |

OTHER PUBLICATIONS

Chemical Abstract No. 121:91772j (Aug. 22, 1994).

*Primary Examiner*—Phyllis G. Spivack
*Attorney, Agent, or Firm*—Dinsmore & Shohl LLP

[57] ABSTRACT

Methods for topical treatment of psoriasis are disclosed comprising applying to the skin a composition comprising an effective amount of a therapeutically active and physiologically acceptable prostaglandin $A_2$, prostaglandin J, derivative of prostaglandin $A_2$, derivative of prostaglandin J, an alkyl ester of prostaglandin A having 1–10 carbons in the alkyl group, or a benzyl ester of prostaglandin A, in a vehicle for topical application. Methods for inhibiting an increased proliferation of cell growth associated with psoriasis in epidermis are further disclosed comprising topically applying to the epidermis an effective amount of a therapeutically active and physiologically acceptable prostaglandin A, prostaglandin J, derivative of prostaglandin A or derivative of prostaglandin J, in a vehicle for topical application.

20 Claims, No Drawings

USE OF PROSTAGLANDINS

Psoriasis is a common dermatologic disorder affecting 1–2% of the population e.g. in Europe and United States. The disease usually debuts between the age of 10–40 years, but may become manifest at any age. Typically hyperkeratotic pink lesions covered by adherent silver-white scales can be found in patients suffering from psoriasis. The lesions have a characteristic shape and are well-demarcated. Not infrequently these lesions are localised to the elbows, knees, the gluteal regions and the scalp and it is generally believed that a cause of the psoriatic lesions is physical contact, pressure e.g. rubbing.

The underlying mechanism of psoriasis is an increased proliferation of cells in the epidermis, primarily the keratinocytes. Thus, the epidermis becomes thick and hyperkeratotic, particularly superficially. The precise mechanism behind the stimulus of the cell proliferation is not known, but generally it is believed that trauma of the skin leads to an inflammatory reaction involving hyperproliferation of keratinocytes in the epidermis. There is a marked genetic disposition to develop psoriasis. Psoriasis may also become generalised over the whole body and psoriasis may cause arthritis, typically in the fingers. Psoriasis may fluctuate but complete and permanent remission is uncommon.

Psoriasis is usually treated with different medications. In simple cases, keratolytics, lubricants and topical corticosteroids are employed. Salicylic acid and anthralin are also used. Another form of medical treatment is PUVA-treatment. PUVA-treatment is based on systemic or local administration of psoralens, e.g. methoxy-psoralen combined with irradiation of the skin with ultraviolet light (UVA). This treatment modality is effective but may predispose to skin cancer. Antimitotics, such as methotrexate, have also been used in severe cases of psoriasis. Although there are presently many treatment modalities for psoriasis there is a definite need for more effective medications with less side-effects.

We have now unexpectedly found that certain prostaglandins may be useful for the treatment of psoriasis. Prostaglandins are fatty acids usually derived from the precursors eicosatrienoic, eicosatetraenoic or eicosapentanoic acid through metabolic steps involving oxygenation. Naturally occurring prostaglandins typically have the general structure

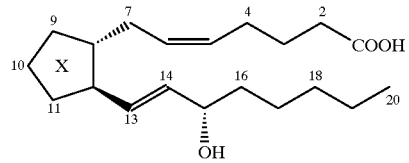

The prostaglandins accordingly carry a cyclopentane ring to which two carbon chains link, the upper usually being called the alpha chain and the lower usually being called the omega chain.

The prostaglandins are classified in subgroups A, B, C, D, E, F and J depending on the structure of the cyclopentane ring:

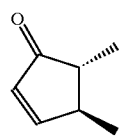
A

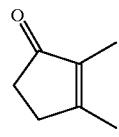
B

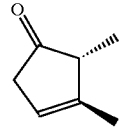
C

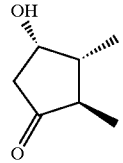
D

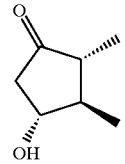
E

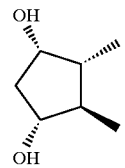
F

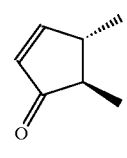
J

The alpha chain is a 7 carbon carboxy-terminated aliphatic chain whereas the omega chain is a 8 carbon methyl-terminated aliphatic chain. Depending on the number of double bonds in these chains subscripts of 1 to 3 are given. In prostaglandins with subscript 1, e.g. $PGA_1$ and $PGJ_1$, the double bond is situated between carbons 13 and 14 in the omega chain, and it exhibits trans configuration in naturally occurring prostaglandins. In prostaglandins with subscript 2, e.g. $PGA_2$ and $PGJ_2$ an additional double bond in the cis configuration exists between carbons 5 and 6 in the alpha chain and finally in prostaglandins with subscript 3 a third double bond is situated between carbons 17 and 18 in the omega chain. This double bond also exhibits cis configuration in naturally occurring prostaglandins. All naturally occurring prostaglandins carry a hydroxyl group in carbon 15, which is essential for biologic activity.

Therapeutic use of prostaglandins for treatment of a great number of various diseases, including psoriasis, has been suggested, especially in patent publications, but no efficient prostaglandin derivative has to be best of our knowledge been presented for treatment of psoriasis.

Prostaglandins to be used according to the present invention are characterized by an α,β-unsaturated cyclopentenone and are in particular of the A and J type in which the cyclopentene ring has the basic structure.

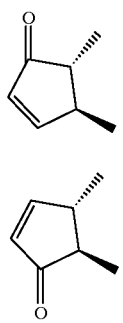

The prostaglandins that have been utilized in the exemplification of the present invention are $PGA_2$ and $PGJ_2$. $PGA_2$ is probably not a naturally occurring prostaglandin in man, but it is formed from PGE2 during acid extraction. $PGJ_2$ on the other hand is a well known metabolite of $PGD_2$, which is a naturally occurring prostaglandin. The molecular structures of $PGA_2$ and $PGJ_2$ are depicted in the figure given below.

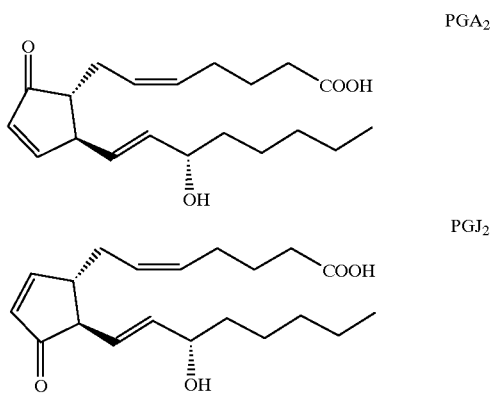

EXEMPLIFICATION OF THE INVENTION

The invention is exemplified with the following non-limiting examples. Prostaglandin $A_2$ ((5Z,13E,15S)-15-hydroxy-9-oxoprosta-5,10,13-trien-1-oic acid) and prostaglandin $J_2$ ((5Z,13E,15S)-15-hydroxy-11-oxoprosta-5,9,13-trien-1-oic acid) were purchased from Cayman Chemical Company (Ann Arbor, Mich., USA) and used in acid form. Both compounds were dissolved in ethanol, and diluted to the final concentration directly in the cell growth medium.

Normal human epidermal keratinocytes (NHEK) derived from foreskin were purchased as secondary cultures (PromoCell, Heidelberg, Germany) and cultured in an optimized ready-to-use serum-free growth medium (KGM medium) (Promocell) at 37° C. in 5% $CO_2$, humidified air. The growth medium is a modification of the MCDB 153 formulation and is supplemented with various concentrations of human epidermal growth factor, insulin, hydrocortisone, bovine pituitary extract and gentamicin/ amphotericin B (proportions proprietary information of Promocell).

For the experiments, cells at passage 3 were used. The effects of the prostaglandins were examined with a photometric cell proliferation assay after 5 days of continuous exposure. Cells were seeded into multiwell tissue culture plates containing KGM medium and quadruplicates of 50 nanomolar to 50 micromolar of the test compounds. KGM medium only, served as control. Every second day the culture medium was exchanged with fresh medium including the appropriate concentration of fresh prostaglandin to provide the cells with sufficient nutrients and to avoid problems that could arise from degradation of the test compound in the culture medium. After 5 days the cells were fixed in glutaraldehyde (1%) and stained by crystal violet (0.1 %) whereupon the stain was eluted by sodium lauryl sulphate (2.5%). The absorbance of the colored solutions, shown to be linearly related to cell number, was monitored photometrically. The experiment was repeated once in its entirety.

The results of the tests are depicted in FIG. 1 and 2. It can be seen that both $PGA_2$ (compound x) and $PGJ_2$ (compound y) markedly inhibited cell growth and reduced the total number of cells. The growth inhibitory effects of the test compounds were noted microscopically after 48 hours, the first time point of observation. For $PGA_2$ (compound x), a decreased cell density but normal cell morphology, as compared to the control, was found in the wells containing 5 micromolar. At 25 and 50 micromolar most cells were still attached to the substratum but all cells were pyknotic, i.e. very small and irregular. For $PGJ_2$ (compound y), a reduction in the number of attached cells but normal cell morphology was found in the wells containing 0.5 micromolar. At 5 micromolar and higher concentrations all cells appeared pyknotic.

After 5 days the growth inhibitory effects of both compounds were even more pronounced (see FIGS. 1 and 2). Both $PGA_2$ (compound x) and $PGJ_2$ (compound y) markedly suppressed growth and reduced the total number of cells in a dose-dependent manner. The highest concentrations tested reduced the cell numbers by 90%. $PGJ_2$ was the most potent compound and exerted a half-maximal growth inhibition at about 0.2 micromolar concentration. The corresponding value of $PGA_2$ was about 1 $\mu$M. The control (compound z) which was the vehicle of the prostaglandin solutions had no effect on cell growth. Thus, both $PGA_2$ and $PGJ_2$ had marked inhibitory effect on the cultured human keratinocytes.

It is accordingly clearly indicated that prostaglandins of the A and J type may be utilized for the treatment of psoriasis. In the exemplification only two prostaglandins, namely $PGA_2$ and $PGJ_2$ were used, but analogues and derivatives of prostaglandins of the A and J type with the same fundamental mechanism of action may also be employed. Analogues of PGA include e.g. 16,16-dimethyl-$PGA_1$, $\Delta^7$-$PGA_1$, $\Delta^7$-$PGA_2$ and 16,16-dimethyl-$PGA_2$.

Analogues or derivatives of PGJ include e.g. $PGJ_1$, $\Delta^{12}PGJ_1$ and $\Delta^{12}PGJ_2$.

There are also other types of derivatives of the A and J type which are known from the literature and which are obvious candidates to be used for treatment according to the present invention. One such group is the derivatives containing a ring substituted omega chain disclosed in PCT application SE89/00475. Also alpha-chain modified prostaglandins may be employed, for instance derivatives containing alkyl substituents.

PGA and PGJ or their analogues may be modified to more lipophilic substances by esterification of different parts of the molecule, e.g., the carboxylic acid moiety. Such esters that may be employed clinically because they penetrate better into the skin, comprise alkyl esters with 1–10 carbon atoms and especially short alkyl esters e.g. methyl, ethyl, and isopropyl or cyclic esters such as benzyl.

The prostaglandin compounds and their esters or derivatives should be used in a suitable vehicle for topical application on the skin. A suitable vehicle includes aqueous vehicles with or without solubilizers, stabilizers such as cyclodextrins, oils, ointments, micelle systems, nanoparticles and various slow release formulations. Such vehicles may or may not contain preservatives depending on whether they are intended for single or multiple use. Various preservatives that may be employed comprise e.g. benzalkonium chloride, chlorhexidine, thiomersal, parabenzoic acid and other compounds with satisfactory antimicrobial effect.

Accordingly, in one aspect of the present invention a formulation containing $PGA_2$ or $PGJ_2$ or derivatives of these prostaglandins is applied topically on the affected skin for different periods of time once or several times daily to treat the psoriatic lesions. Such treatment may take only a few weeks or may go on for longer times depending on the clinical situation. The recommended dose to be used depends on the particular prostaglandin and its physical-chemical characteristics but is usually in the range of from 0.01 to 100 μg per application. On an area of 1 $dm^2$ typically a dose of 0.1–10 μg per application is employed. The medication can be instilled once or several times daily depending on the clinical situation, and the dosage form. When the psoriatic lesion has regressed treatment may continue intermittently or may be terminated.

The invention also relates to the use of a a prostaglandin derivative as defined above for the preparation of a composition for treatment of psoriasis.

We claim:

1. A method for topical treatment of psoriasis, comprising applying to the skin a composition comprising an effective amount of a therapeutically active and physiologically acceptable prostaglandin $A_2$, prostaglandin J, derivative of prostaglandin $A_2$, derivative of prostaglandin J, an alkyl ester of prostaglandin A having 1–10 carbons in the alkyl group, or a benzyl ester of prostaglandin A, in a vehicle for topical application.

2. A method according to claim 1, wherein the composition comprises a prostaglandin $A_2$, or a derivative thereof.

3. A method according to claim 1, wherein the composition comprises an alkyl ester of a PGA having 1–10 carbons in the alkyl group or a benzyl ester of a PGA, or a derivative thereof.

4. A method according to claim 1, wherein the composition comprises a methyl, ethyl or isopropyl ester of a PGA, or a derivative thereof.

5. A method according to claim 1, wherein the composition comprises an isopropyl ester of a PGA, or a derivative thereof.

6. A method according to claim 1, wherein the composition comprises a prostaglandin J or a derivative thereof.

7. A method according to claim 6, wherein the composition comprises $PGJ_1$, $PGJ_2$, $\Delta^{12}PGJ_1$, $\Delta^{12}PGJ_2$, a ring-substituted omega chain PGJ, an alkyl-substituted alpha chain PGJ, or a PGJ ester, or a derivative thereof.

8. A method according to claim 6, wherein the composition comprises an alkyl ester of a PGJ having 1–10 carbons in the alkyl group or a benzyl ester of a PGJ, or a derivative thereof.

9. A method according to claim 6, wherein the composition comprises a methyl, ethyl or isopropyl ester of a PGJ, or a derivative thereof.

10. A method according to claim 6, wherein the composition comprises an isopropyl ester of a PGJ, or a derivative thereof.

11. A method according to claim 1, wherein the composition is applied in an amount sufficient to apply from 0.01 to 100 μg of a prostaglandin $A_2$, prostaglandin J, derivative of prostaglandin $A_2$, derivative of prostaglandin J, alkyl ester of prostaglandin A having 1–10 carbons in the alkyl group, or benzyl ester of prostaglandin A.

12. A method according to claim 1, wherein the composition is applied in an amount sufficient to apply from 0.1 to 10 μg of a prostaglandin $A_2$, prostaglandin J, derivative of prostaglandin $A_2$, derivative of prostaglandin J, alkyl ester of prostaglandin A having 1–10 carbons in the alkyl group, or benzyl ester of prostaglandin A.

13. A method according to claim 1, wherein the vehicle comprises an aqueous vehicle and the composition further comprises a preservative.

14. A method according to claim 1, wherein the composition comprises $PGA_2$, 16,16-dimethyl-$PGA_2$,$\Delta^7$-$PGA_2$, or a derivative thereof.

15. A method for inhibiting an increased proliferation of cell growth associated with psoriasis in epidermis, comprising topically applying to the epidermis an effective amount of a therapeutically active and physiologically acceptable prostaglandin A, prostaglandin J, derivative of prostaglandin A or derivative of prostaglandin J, in a vehicle for topical application.

16. A method according to claim 15, wherein the composition comprises a prostaglandin A or a derivative thereof.

17. A method according to claim 16, wherein the composition comprises an alkyl ester of a prostaglandin A having 1–10 carbons in the alkyl group or a benzyl ester of a prostaglandin A, or a derivative thereof.

18. A method according to claim 15, wherein the composition comprises a prostaglandin J or a derivative thereof.

19. A method according to claim 18, wherein the composition comprises an alkyl ester of a prostaglandin J having 1–10 carbons in the alkyl group or a benzyl ester of a prostaglandin J, or a derivative thereof.

20. A method according to claim 15, wherein the composition is applied in an amount sufficient to apply from 0.01 to 100 μg of a prostaglandin A, prostaglandin J or derivative thereof.

* * * * *

UNITED STATES PATENT AND TRADEMARK OFFICE
CERTIFICATE OF CORRECTION

PATENT NO. : 6,031,001
DATED : February 29, 2001
INVENTOR(S) : Johan Stjernschantz et al.

It is certified that error appears in the above-identified patent and that said Letters Patent is hereby corrected as shown below:

Claim 12, column 6, line 26, after "A", insert --per $dm^2$ of skin surface--.

Signed and Sealed this

Sixth Day of February, 2001

Attest:

Q. TODD DICKINSON

Attesting Officer

Director of Patents and Trademarks